United States Patent
Scott et al.

(10) Patent No.: US 11,406,775 B2
(45) Date of Patent: Aug. 9, 2022

(54) INHALER APPARATUS

(71) Applicant: NERUDIA LIMITED, Liverpool (GB)

(72) Inventors: Kenneth Scott, Liverpool (GB); Tom Sudlow, Liverpool (GB); Christopher Lord, Liverpool (GB); Stephen McDonald, Liverpool (GB); David Jones, Liverpool (GB)

(73) Assignee: Nerudia Limited, Liverpool (GB)

( * ) Notice: Subject to any disclaimer, the term of this patent is extended or adjusted under 35 U.S.C. 154(b) by 0 days.

(21) Appl. No.: 15/755,241

(22) PCT Filed: Aug. 25, 2016

(86) PCT No.: PCT/GB2016/052648
§ 371 (c)(1),
(2) Date: Feb. 26, 2018

(87) PCT Pub. No.: WO2017/033021
PCT Pub. Date: Mar. 2, 2017

(65) Prior Publication Data
US 2018/0220708 A1 Aug. 9, 2018

(30) Foreign Application Priority Data
Aug. 27, 2015 (GB) ...................... 1515274

(51) Int. Cl.
A61M 15/06 (2006.01)
A61M 11/04 (2006.01)
(Continued)

(52) U.S. Cl.
CPC ........... *A61M 15/06* (2013.01); *A24B 15/167* (2016.11); *A24B 15/283* (2013.01); *A24F 40/46* (2020.01);
(Continued)

(58) Field of Classification Search
CPC .... A24F 47/008; A24F 47/006; A24F 47/004; A24B 15/283; A24B 15/167;
(Continued)

(56) References Cited

U.S. PATENT DOCUMENTS 4,137,914 A * 2/1979 Wetterlin .......... A61M 15/0036
128/200.23
5,683,361 A * 11/1997 Elk .................... A61M 15/0028
604/58

(Continued)

FOREIGN PATENT DOCUMENTS

CN 101568269 A 10/2009
CN 103997921 A 8/2014
(Continued)

OTHER PUBLICATIONS

UKIPO Combined Search and Examination Report in GB Application No. GB 1515274.7, dated Dec. 9, 2016, 9 pages.
(Continued)

*Primary Examiner* — Joseph S Del Sole
*Assistant Examiner* — Baileigh Kate Darnell
(74) *Attorney, Agent, or Firm* — Sheppard Mullin Richter & Hampton LLP

(57) ABSTRACT

The present invention relates to an inhaler comprising: an assembly including a heater element arranged in the inhaler to be proximal to a substrate region configured for supporting a vapour or atomiser precursor substrate; wherein the assembly is configured such that the heater element is operative to achieve and maintain a target temperature in the substrate region throughout a period corresponding to a plurality of consecutive uses of the inhaler.

30 Claims, 4 Drawing Sheets

(51) Int. Cl.
*A24F 40/46* (2020.01)
*A24F 40/51* (2020.01)
*A24F 42/60* (2020.01)
*A24F 42/10* (2020.01)
*A24B 15/167* (2020.01)
*A24B 15/28* (2006.01)
*H05B 1/02* (2006.01)
*A61M 15/00* (2006.01)
*A24F 40/10* (2020.01)

(52) U.S. Cl.
CPC .............. *A24F 40/51* (2020.01); *A24F 42/10* (2020.01); *A24F 42/60* (2020.01); *A61M 11/042* (2014.02); *A61M 11/047* (2014.02); *H05B 1/0213* (2013.01); *H05B 1/0297* (2013.01); *A24F 40/10* (2020.01); *A61M 15/0028* (2013.01); *A61M 2205/3368* (2013.01); *A61M 2205/364* (2013.01); *A61M 2205/3653* (2013.01); *A61M 2205/8206* (2013.01)

(58) Field of Classification Search
CPC .. A61M 11/042; A61M 11/047; A61M 11/06; A61M 11/0028; A61M 2205/8206; A61M 2205/3653; A61M 2205/364; A61M 2205/3368; H05B 1/0297; H05B 1/0213
See application file for complete search history.

(56) References Cited

U.S. PATENT DOCUMENTS

| | | | | |
|---|---|---|---|---|
| 8,739,788 | B2 * | 6/2014 | Yomtov | A61M 11/041 128/203.26 |
| 10,076,140 | B2 * | 9/2018 | Silvestrini | A24F 47/008 |
| 2004/0099266 | A1 * | 5/2004 | Cross | A61M 11/041 128/203.12 |
| 2004/0236282 | A1 * | 11/2004 | Braithwaite | A61M 15/0036 604/158 |
| 2005/0016549 | A1 * | 1/2005 | Banerjee | A24B 15/16 131/194 |
| 2009/0151717 | A1 | 6/2009 | Bowen | |
| 2010/0006113 | A1 * | 1/2010 | Urtsev | A24F 47/008 131/273 |
| 2012/0152244 | A1 * | 6/2012 | Yomtov | A61M 11/041 128/203.14 |
| 2012/0204889 | A1 | 8/2012 | Xiu | |
| 2014/0346689 | A1 * | 11/2014 | Dubief | A24F 47/008 261/142 |
| 2015/0223520 | A1 * | 8/2015 | Phillips | A61M 15/06 131/328 |
| 2017/0006917 | A1 * | 1/2017 | Alvarez | A24F 47/008 |
| 2017/0095002 | A1 * | 4/2017 | Silvestrini | A24F 47/008 |

FOREIGN PATENT DOCUMENTS

| | | |
|---|---|---|
| CN | 104602555 A | 5/2015 |
| CN | 104720119 A | 6/2015 |
| CN | 204440192 U | 7/2015 |
| WO | 2013098398 A2 | 7/2013 |
| WO | 2014040988 A2 | 3/2014 |
| WO | 2014045025 A2 | 3/2014 |
| WO | 2014150247 A1 | 9/2014 |
| WO | 2015175979 A1 | 11/2015 |
| WO | 2015197627 A1 | 12/2015 |
| WO | 2016166064 A1 | 10/2016 |

OTHER PUBLICATIONS

International Search Report and Written Opinion in International Application No. PCT/GB2016/052648, dated Nov. 9, 2016, 10 pages.
Chinese Search Report in Chinese Application No. 201680049675.2, dated Apr. 3, 2020, 11 pages.
European Search Report in European Application No. 16758250.1, dated Apr. 2, 2020, 6 pages.

* cited by examiner

INHALER APPARATUS

CROSS-REFERENCE TO RELATED APPLICATIONS

This application is a National Phase application under 35 U.S.C. § 371 of PCT Application No. PCT/GB2016/052648, filed Aug. 25, 2016, which application claims priority benefit to Great Britain Application No. 1515274.7, filed Aug. 27, 2015, the entire contents of which applications are hereby incorporated herein by reference.

FIELD

The present invention relates to an inhaler apparatus, in particular but not exclusively to an inhaler apparatus configured for use as a smoking substitute device.

BACKGROUND

Various inhaler apparatus are known for delivering drug formulations or the like in atomised or vaporised form or in a carrier medium such as a vapour to a user by inhalation through the mouth or nose. A particular example is the Nicorette® inhalator (trade name) used for the oral delivery through inhalation of nicotine. The Nicorette® inhalator comprises a main body having a mouthpiece through which a user can inhale. The main body has an opening at the end opposite the mouthpiece, into which may be inserted a capsule containing a substrate impregnated with nicotine. The capsule has a frangible seal at both ends. The capsule may be impaled at one end on a hollow cylindrical prong disposed in the main body so as to rupture the frangible seal at that end and provide fluid communication between the interior of the capsule and the mouthpiece. The Nicorette® inhalator also has an end piece configured to connect to the opening at the end of the main body opposite the mouthpiece. The end piece also includes a hollow cylindrical prong which is in fluid communication with an inlet at an end of the end piece opposite to that which connects to the main body. The inhalator is configured such that when the end piece is connected to the main body a frangible seal at the other end of the capsule is ruptured thereby also providing fluid communication between the inlet of the end piece and the capsule. Therefore, when the end piece is connected a fluid pathway for air is established between the inlet and the mouthpiece, which passes through the capsule. When a user inhales through the mouthpiece, air is drawn over the nicotine impregnated substrate such that particles of nicotine or nicotine carrying medium may be atomised and delivered to a user's respiratory system.

A user of a Nicorette® inhalator may simply inhale or "puff" as often as they like until such time as they no longer receive any nicotine or insufficient nicotine to satisfy their preferences.

There are also known so-called "vaping" devices in which a liquid, which may or may not contain nicotine, is brought into contact with a heating coil to vaporise and/or atomise the liquid so that it may be inhaled.

Aspects and embodiments in accordance with the present invention were devised with the foregoing in mind.

SUMMARY

Viewed from a first aspect there is provided an inhaler comprising an assembly including a heater element arranged in the inhaler to be proximal to a substrate region configured for supporting a vapour or atomiser precursor substrate. The assembly is configured such that the heater element is operative to achieve and maintain a target temperature in the substrate region throughout a period corresponding to a plurality of consecutive uses of the inhaler.

An inhaler in accordance with the first aspect of the present invention may maintain a substrate region, and hence a substrate in such a region, at a target temperature suitable for activating a vapour or atomising a material supported by the substrate for inhalation by a user of the inhaler. Maintaining the substrate at the target temperature may allow operation of the inhaler at a lower temperature than would otherwise be the case and/or obviate the need for a user to keep pressing a button or other user actuable input the activate the heater element.

In an embodiment of the present invention, the heater element is an electrical heater element. Electrical heater elements are relatively simple to activate and control and can be obtained is sizes suitable for inclusion in a hand-held inhaler device.

An embodiment in accordance with the present invention may comprise a temperature controllable switch configured to control the heater element to achieve and maintain the target temperature throughout the period. In this way, the heater element may be controlled, e.g. by controlling the supply of current to it, to maintain the desired temperature.

In an embodiment in accordance with the present invention, the assembly may further comprise a temperature sensor operative to provide a signal to the temperature controllable switch indicative of a temperature in the substrate region. The temperature sensor may be separate from the temperature controllable switch which permits it to be placed at a suitable location in the substrate region. Optionally, the assembly is configured such that the temperature controllable switch is integral with the temperature sensor.

Suitably, the temperature sensor is a one of a thermistor, thermocouple and resistance temperature detector (RTD) which are readily available sensors and may be sized suitable for inclusion in a hand-held inhaler.

In an embodiment in accordance with the present invention, the temperature controllable switch is operative to couple and/or decouple the heater element from an electrical current source to achieve and maintain the target temperature throughout the period. This is a particularly simple way of controlling the heater element.

The temperature controllable switch may comprise a bi-metal strip or an electrical switch.

In an embodiment in accordance with the present invention, the inhaler is configured to receive and support a capsule in which a substrate is enclosed. The capsule may protect the substrate from contamination and is a convenient way of supporting the substrate so space should be made for a capsule in the inhaler. In an embodiment configured to receive a capsule the assembly is arranged such the heater element is disposed proximal to where a capsule is to be supported in the inhaler thereby to effect heating of the substrate.

In an embodiment in accordance with the present invention, wherein the heater element is arranged to define an interior space into which the substrate may be inserted. Optionally, the heater element is arranged to define an interior space into which the capsule may be inserted. Such a configuration may allow for the substrate to be heated substantially evenly. A suitable configuration is for the heater element is in the shape of an open helical coil having an internal diameter sufficiently large for a substrate or capsule may be inserted between the coils.

In an embodiment in accordance with the present invention, the heater element may comprise a partitioned container respective partitions comprising constituent elements which when brought together create an exothermic reaction. Such a chemical heating arrangement obviates the need for electrical heating and therefore an electrical power supply.

The assembly may be arranged such that temperature sensor is disposed proximal to where a capsule is to be supported in the inhaler so that the temperature in an around the substrate may be monitored.

In an embodiment in accordance with the present invention, there is provided a current source for example a battery. Suitably, the assembly comprises the current source. The current source is typically an electrical battery.

In an embodiment in accordance with the present invention, the assembly is configured such that the period lies in the range 2 minutes to 8 minutes, particularly in the range 3 minutes to 6 minutes and more particularly in the range 4 minutes to 5 minutes. Such periods allow for the inhaler to be used to inhale, be placed down and then used again a little while later without the user having to activate or reactivate the heater element.

In an embodiment in accordance with the present invention, the assembly is configured such that the heater element is operative to achieve and maintain the target temperature in the range from 20° C. to 50° C., in particular from 30° C. to 50° C., more particularly from 35° C. to 45° C., yet more particularly 35° C. to 40° C. Such a temperature range is suitable for maintaining over a period of time without overheating the inhaler and enhances the vaporisation and/or atomisation of the substance on the substrate compared to use at ambient room temperature.

In an embodiment in accordance with the present invention, the assembly is configured such that the heater element is responsive to an input to initiate heating of the substrate region to the target temperature. Typically, the input is a manual input. A manual input such as the pressing of a switch or the twist of a cylinder may provide a satisfactory tactile interaction with the inhaler for the user such as may be experienced when smoking a cigarette.

Suitably, an embodiment in accordance with the present invention provides an assembly in accordance with the assembly of the inhaler of any preceding claim. Such an assembly may be a spare or replacement part for the inhaler or an item used in the manufacture of the inhaler.

Viewed from another aspect, the substrate may comprise a vapour and/or atomiser precursor comprising one or more of nicotine, a nicotine derivative and nicotine analogue. Additionally, the vapour and/or atomiser precursor may comprise one or more of a glycol, polyglycol and water.

Suitably, the substrate is hydrophilic particularly if the precursor comprises water.

The substrate may comprise a sintered material which may enhance sorption of the precursor. A typical substrate may comprise a polypropylene or polyethylene terephthalate.

In yet another aspect there is provided a capsule for an inhaler. The capsule may enclose a substrate such as defined above.

The inhaler may comprise a substrate as defined above or a capsule as defined above.

Viewed from a yet further aspect there is provided a vapour and/or atomiser inhaler device comprising an inhaler such as defined above. Such a vapour and/or inhaler device may be operative as a smoking substitute device. For a device operative as a smoking substitute device the period corresponds to the typical time for a person to smoke a cigarette.

LIST OF FIGURES

One or more specific embodiments of the present invention will now be described, by way of non-limiting example only, with reference to the following drawings, in which.

DESCRIPTION

In general outline, embodiments in accordance with the present invention provide an inhaler apparatus in which a nicotine supporting substrate may be inserted and a fluid pathway for air is established between an inlet and a mouthpiece, which fluid pathway directs air past the nicotine supporting substrate. A heater element is provided for the inhaler apparatus where the heater element is arranged in the inhaler apparatus such that a region around and proximal to where the substrate may be inserted may be heated by the heater element. In the following described embodiment, the heater element is part of an assembly comprising circuitry for controlling the heater element such that it may achieve and maintain a desired target temperature in the region proximal to the substrate, the amount of heat generated by the heater element being controlled to maintain the target temperature.

Figure 1:
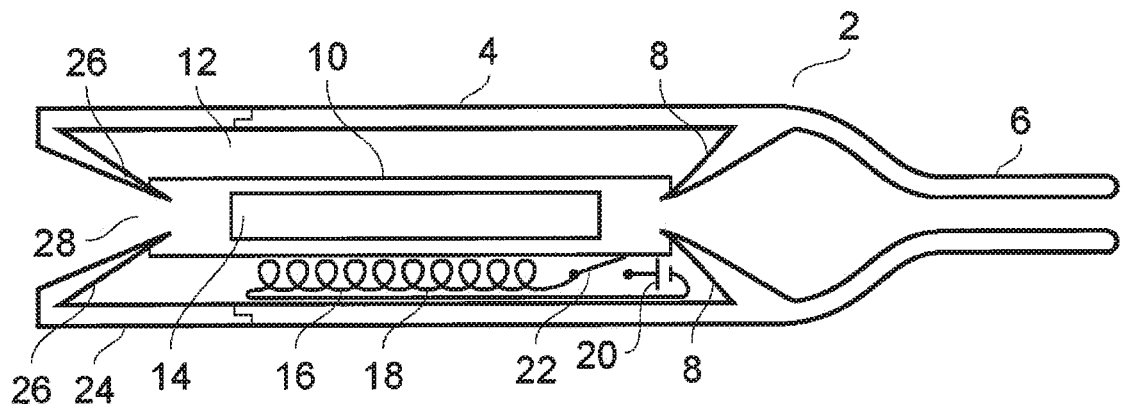
FIG. 1 is a schematic illustration of an inhaler in accordance with a first embodiment in accordance with the present invention seen in a side view.

Referring now to FIG. 1, there is a schematic illustration of an inhaler apparatus 2 comprising a main body 4 and having a mouthpiece 6 at one end thereof. Prongs 8 are provided "upstream" of mouthpiece 6 and are configured to rupture an end seal of a capsule 10 which may be delivered into the main body through an aperture 12 at an end of the main body upstream of the mouthpiece 6. For the avoidance of doubt, the term "upstream" defines a position towards the point at which a fluid will be drawn into the apparatus 2 when it is in use, i.e. a point from which air is drawn into the apparatus via aperture 12 towards the mouthpiece 6.

The capsule 10 houses a substrate 14 impregnated with a vapour and/or atomiser nicotine containing precursor to form a pharmaceutically acceptable source of nicotine for oral or nasal delivery by inhalation.

The main body 4 includes a heater assembly 16 comprising a heater coil 18 and a 3V lithium battery 20 as a power source. Additionally, the heater assembly 16 also comprises a temperature controllable switch 22 which is arranged to couple and decouple heater coil 18 from battery 20 depending on whether the temperature in the capsule region of the apparatus 2 is below or above a threshold temperature.

The apparatus 2 also comprises an end piece 24 which has end prongs 26 defining an end piece aperture 28. End piece 24 is configured to push fit onto main body 4 and rupture an upstream end seal of capsule 10 thereby providing a fluid conduit from end piece aperture 28 through capsule 10 to mouthpiece 6.

In the described embodiment the precursor is in liquid form and may comprise one or more of a glycol, polyglycol and water. Also, the precursor comprises nicotine and/or a nicotine derivative and/or an analogue of nicotine. The precursor is sorbed into, typically, polypropylene or polyethylene terephthalate, which forms the substrate material 14.

In the described embodiment, each capsule 10 comprises 2 mg of nicotine. The nicotine may be mixed with another ingredient, for example menthol, to mask the taste of the nicotine, which tastes unpleasant in its pure form. An example mixture comprises 80% pure nicotine and 20% menthol. An advantage of menthol is that it may anaesthetise the throat to make the nicotine more palatable.

Figure 2:
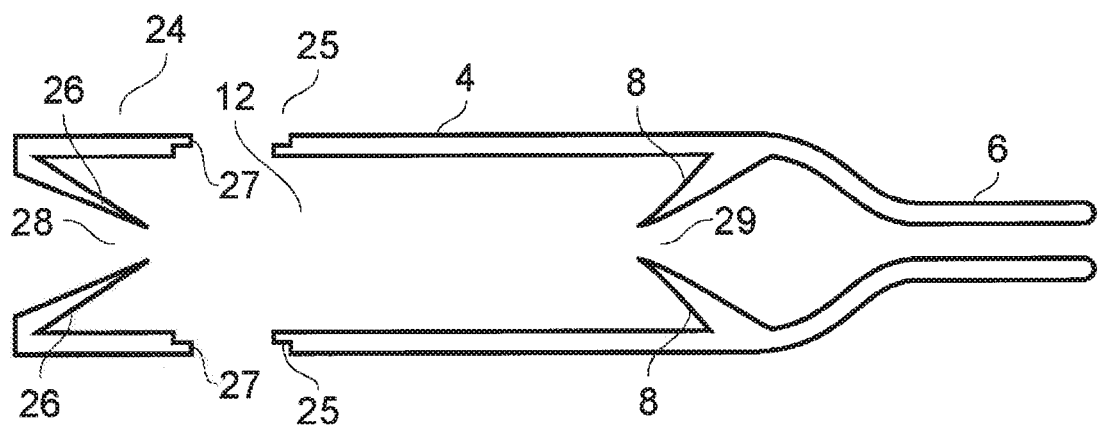
FIG. 2 is a cross-sectional view of an inhaler in accordance with a first embodiment of the present invention is schematically illustrating the location of the heater assembly.

Turning now to FIG. 2, a side view of an inhaler is schematically illustrated showing the main body 4 and end piece 24 separate from each other. The main body 4 has a reduced diameter section 25 for cooperating with the overlap sections 27 on the end piece 24 to form the push fit arrangement. As is clearly illustrated, prongs 8 define an aperture 29 through which a vaporised and/or atomised substance sorbed into the substrate 14 may be drawn into mouthpiece 6. Likewise, prongs 26 in the end piece 24 define an aperture 28 through which air may be drawn into the inhaler 2 and over a substrate 14 when a capsule 10 is supported within the inhaler 2. The aperture therefore provides an inlet to the apparatus for the air.

Figure 3:
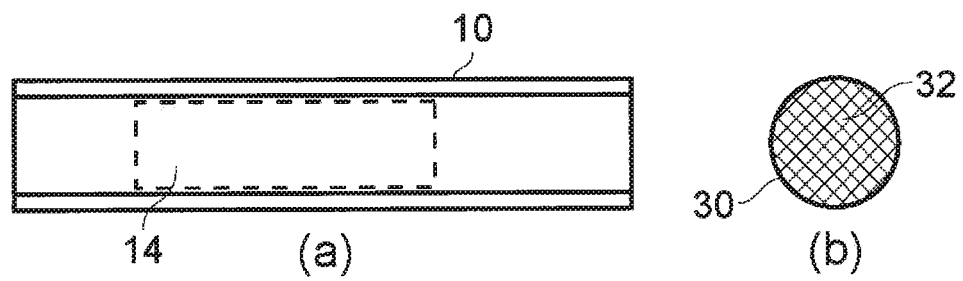
FIG. 3(a) is a cross-sectional view of a capsule containing a nicotine supporting substrate.
FIG. 3(b) is an end view of the capsule illustrated in FIG. 3(a)

FIG. 3(*a*) schematically illustrates a cross-sectional view of a capsule 10 in which is supported substrate 14. The capsule is cylindrical as can be seen from the end view in FIG. 3(*b*) and the substrate 14 is substantially cylindrical to extend to the interior walls of the capsule 10. Each end 30 of the capsule 10 is sealed with a rupturable film 32 which in the described embodiment is a metallised film, i.e. aluminium film.

Figure 4:
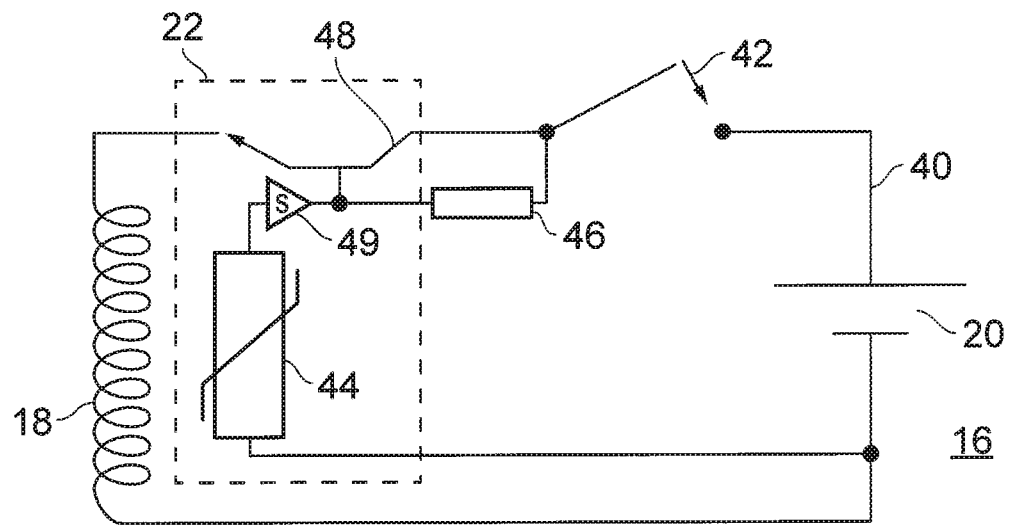
FIG. 4 is a schematic circuit diagram of a heater assembly in accordance with an embodiment of the present invention.

Turning now to FIG. 4, a schematic circuit diagram 40 of a heater assembly 16 in accordance with an embodiment of the present invention is illustrated. Heater coil 18 is coupled to a temperature controllable switch 22, illustrated in dotted outline, and a negative terminal of battery 20. The temperature controllable switch 22 comprises a temperature sensor 44 which in the described embodiment is a thermistor coupled between the terminals of battery 20 through a resistor 46. A terminal of thermistor 44 is coupled to the base of transistor 48, through a Schmitt trigger 49, which provides a base current to the transistor 48 to switch the transistor between conducting an non-conducting mode of operation in dependence upon the voltage across the thermistor 44 which is dependent upon the temperature of the region in which the thermistor is placed. The thermistor 44 and transistor 48 form the temperature controllable switch 22.

In an optional embodiment, temperature controllable switch 22 may be formed of a bimetallic strip to switch the battery 20 into connectivity with heating coil 18.

The temperature controllable switch 22 is connected to the battery 20 through a single throw single pole switch 42. Switch 42 is open prior to actuation and when closed connects thermistor 44 to battery 20. Depending upon the temperature, the voltage drop across thermistor 44 is sufficient to close switch transistor 48, i.e. turn it into its conducting state, in order to provide current to heating coil 18. As heating coil 18 heats the surrounding region so heating thermistor 44, the voltage across thermistor 44 changes in accordance with the temperature such that switch transistor 48 is opened, i.e. turned into its non-conducting state thereby courting current supply to heating coil 18. Consequently, in the absence of a current to heating coil 18 the temperature in the region surrounding the heating coil decreases thereby changing the voltage across thermistor 44 such that switch transistor 48 is closed and current flows to the heating coil 18. In this way, the temperature in a region surrounding the heating coil 18 may be maintained at or around a target temperature by the switching on and off of current to the heating coil 18.

Switch 42 they be a simple toggle switch in which repeated actuation switches it from a nonconducting state to a conducting state and back again to a non-conducting state.

In an inhaler device in accordance with a particular embodiment of the present invention, the heating assembly is arranged such that an actuating member for switch 42 is accessible through the wall of the main body 4 of the inhaler device. For example, the actuating member may protrude through the wall by suitable sealing material such as silicone film. Optionally, the actuating member may be within the main body 4 of the inhaler and actuable by depression of a wall of the main body 4 onto the actuating member. In such an embodiment the region of the main body 4 depressed onto the actuating member may be of a thinner material than the rest of the main body 4 such that it may be depressed onto the actuating member or is of a resilient compressible material such as a rubber.

In one embodiment in accordance with the present invention the inhaler device 2 may be configured as a smoking substitute device in which instance the capsule will contain a substrate having sorbed nicotine, a nicotine derivative and/or or a nicotine analogue in an excipient such as water, and/or glycol and/or polyglycol. The shape and configuration of inhaler 2 is such that it mimics a cigarette and the bringing the inhaler to the mouth inhaling and exhaling mimics how a smoker smokes a cigarette. In this way, the inhaler may assist a smoker to satisfy the physical habits developed when smoking cigarettes and therefore provide a more satisfactory experience than would otherwise be the case. Typically, a cigarette lasts for between 4 to 6 minutes from the time it is lit until the time the tobacco is exhausted or a smoker considers sufficient nicotine laden smoke has been inhaled that they may extinguish the cigarette. The smoker may actuate switch 42 so that they may obtain a smoking experience from the inhaler and after a period of time typical to that smoking cigarette they may actuate switch 42 again to decouple temperature controllable switch 22 from battery 20. Optionally, battery 20 may be a rechargeable battery which has a maximum charge that is typically discharged over a period of a few minutes before the current from the battery 20 is too low to effect sufficient heating of the coil 18 or to activate thermistor 44 to maintain switch 48 open such that switch 48 automatically closes. Thus, the user no longer receives any nicotine effect from inhalation and consequently ceases the smoking substitute activity. Typically, the user will then connect battery 20 to a battery charger so that the inhaler may be used again once the battery has been recharged.

In one embodiment, it is envisaged that the heater assembly utilises a heating coil from or is a cartridge heater coil. In one embodiment, the cartridge heater coil may be from a low voltage cartridge heater such as a ⅛ inch (3.175 mm) diameter 1 inch (25.4 mm) long high density cartridge heater 12V/7.5 W, part number MCH2-30W-001 supplied by Comstat, Inc. In order to obtain a heating effect to raise the temperature in the region of the capsule to one effective to produce an aerosol size having a particularly good deep lung penetration and/or pharmacological effect on a user, the current supplied to the coil must be sufficient for the region around the capsule to be heated to around 37° C.-42° C. In one embodiment, a 3.6 V rechargeable lithium battery such as a 2032 button battery is utilised. For a smaller and slimmer configuration of inhaler a coin type lithium manganese dioxide 2.5 V rechargeable battery, product code ML 1220 available from Hitachi Maxell, Ltd may be used as battery 20.

In an embodiment configured as a smoking substitute device, switch 42 is configured as a timer switch such that it opens to decouple temperature controllable switch 22 from battery 20 after a period of time similar to that usually taken to smoke a cigarette, i.e. between 4 to 6 minutes from when the switch 42 is actuated to close and couple temperature controllable switch 22 to battery 20. The timer circuitry may comprise an RC circuit coupled to switch 22 to provide a voltage signal of a sufficient level to open the switch after the desired time period. Other forms of electronic or electrical timer may be employed.

Figure 6:
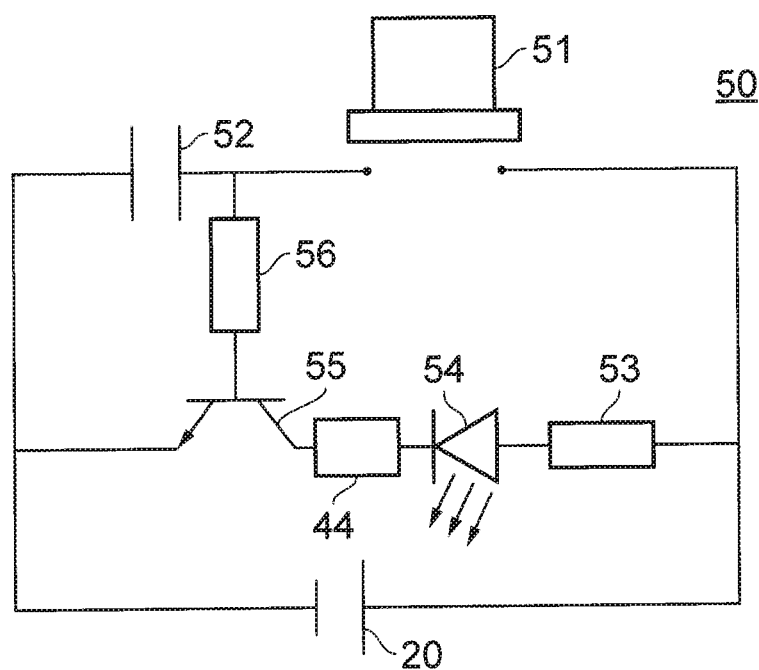
FIG. 6 is a schematic circuit diagram of a pushbutton timer delay circuit in accordance with an embodiment of the present invention.

In one or more embodiments, switch 42 may be configured as a pushbutton electronic timer circuit 50 such as schematically illustrated in FIG. 6. The pushbutton electronic timer circuit 50 comprises a returnable pushbutton 51 which initiates the timing circuitry. The polls of pushbutton 51 between the terminals of battery 20 and in series with a capacitor 52. Typically the capacitor is of a few thousand microfarads (~1000 μF) depending upon the amount of delay required. In parallel with the pushbutton 51 and capacitor 52 is a transistor switch 55 in series with a light emitting diode 54 and resistor 53. The base of the transistor switch 55 is coupled to a point between the capacitor 52 and pushbutton switch 51 via a resistor 56.

Initiation of the timing circuitry is achieved by depressing pushbutton 51 which supplies a positive voltage from battery 22 based resistor 56 to switch on transistor 55. When transistor 55 is switched on current flows through LED 54 which emits light. At the same time, capacitor 52 is charged. When the pushbutton is released such that it may return to an open position the voltage to the base transistor 56 is disconnected but the transistor 55 is still able to conduct due to the stored energy in a capacitor providing a voltage across based resistor 56. The capacitor gradually discharges through base resistor 56 and transistor 55 causing the LED 54 and thermistor 44 to continue to receive current, i.e. be switched on. When the capacitor 52 is to show sufficiently for the voltage across based assistive 56 to fall below the threshold voltage and turn the transistor switch 55 off, no longer flows through thermistor 44 and LED 54. The value of the capacitor substantially determines the time delay or how long the transistor switch 55 is conducting and therefore the thermistor 44 is active and can control resistor switch 48 of the heater circuitry 40 illustrated in FIG. 4.

LED 54 is illustrated as an optional extra and need not be incorporated in the circuitry for it to achieve its timing function. However, LED 54 may be usefully employed in an embodiment utilising a pushbutton electronic timer circuit 54 for switch 42 as it would indicate to a user when the power supply to the heating coil is removed. Therefore, if the value of capacitor 52 is chosen to provide a time delay of around five minutes a user will have a typical smoking period in which to satisfy their smoking desire utilising the inhaler and have a clear indication of when the typical time period is up because the LED 54 is no longer emitting light.

In another embodiment, switch 42 may be of a type known as a pneumatic time delay pushbutton switch which utilises the gradual release of a pressure to move a switch from an on position to an off position.

Figure 5:
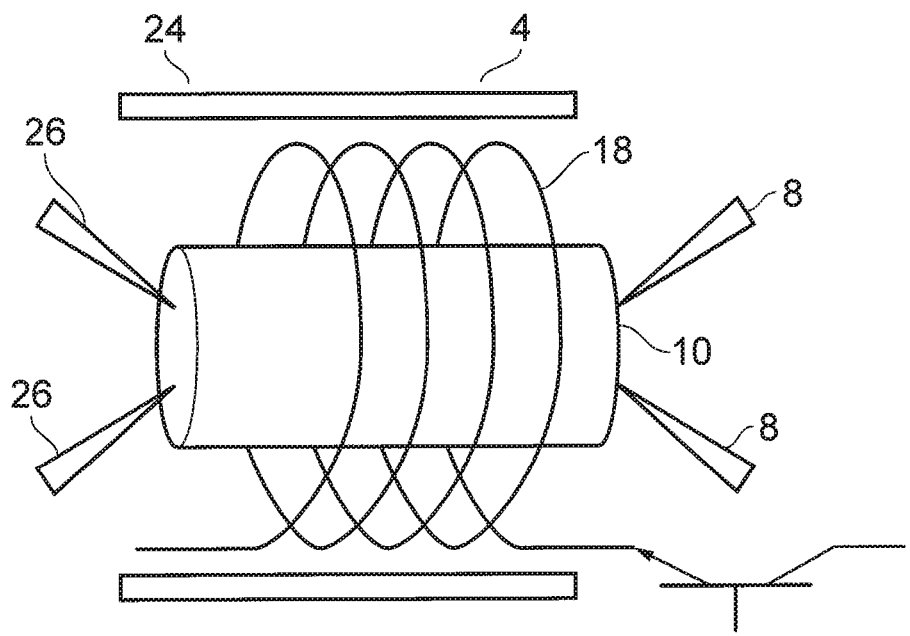
FIG. 5 is a diagrammatic illustration of a heater assembly comprising chemical coil heater element configured to provide a space in which a substrate capsule may be inserted in accordance with an embodiment of the present invention.

In an optional embodiment, heating coil 18 is configured to provide a space within the main body 4 into which a capsule 10 may be inserted. Such an embodiment is illustrated in FIG. 5 in which heating coil 18 is configured such that the coils extend toward the inner wall of the main body 4 and provide a space substantially along a longitudinal axis of the main body 4 into which the capsule 10 may be inserted. In such an embodiment, substantially even heating of the capsule 10 may be achieved.

Figure 7:
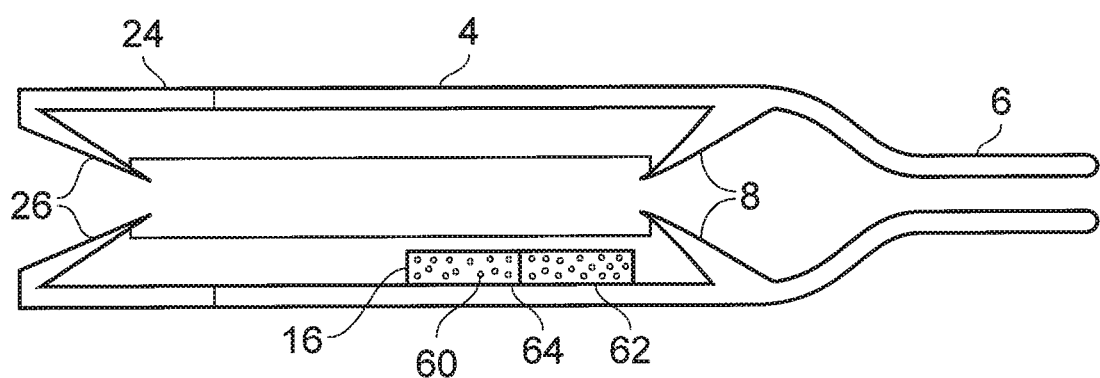
FIG. 7 is a diagrammatic illustration of an inhaler incorporating a heater assembly comprising separated constituent compounds for creating an exothermic reaction in accordance with an embodiment of the present invention.

In a yet further embodiment, chemical heating is used instead of electrical heating. Referring now to FIG. 7 a simple schematic illustration of an inhaler in accordance with an embodiment of the present invention is provided showing the main body 4 having mouthpiece 6, prongs 8 and 26, end piece 24 and capsule 10. Heating assembly 16 is illustrated as a container partitioned into two parts, 60 and 62 separated by a frangible membrane 64. The heating assembly is supported adjacent an inner wall of the main body 4. In part 60 there is a 10 mL saturated solution of sodium bicarbonate and in part 62 about 2.5 mL of calcium chloride. The wall of the main body 4 in the region of the heater assembly 16 is configured by filling or by treating the material or including a specific type of material that allow pressure to be put on heater assembly 16 so that frangible membrane 64 may be ruptured and the sodium bicarbonate solution and calcium chloride are mixed together. The mixing effect may be enhanced by shaking the inhaler. The exothermic reaction will cause mild heating of the interior of the inhaler and increases temperature by around 15° C.-20° C. thereby taking the temperature from a typical room temperature of 20° C. to a temperature of between 35° C. and 40° C. The duration of the heating and temperature will depend upon the amount of sodium bicarbonate solution and calcium chloride in respective partitions 60 and 62.

As used herein any reference to "one embodiment" or "an embodiment" means that a particular element, feature, structure, or characteristic described in connection with the embodiment is included in at least one embodiment. The appearances of the phrase "in one embodiment" or the phrase "in an embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the invention. This is done merely for convenience and to give a general sense of the invention.

This description should be read to include one or at least one and the singular also includes the plural unless it is obvious that it is meant otherwise.

In view of the foregoing description it will be evident to a person skilled in the art that various modifications may be made within the scope of the invention. For example, in the described embodiment the end piece is push fitted onto the main body but may optionally be a "snap fit" engagement or a simple "twist & lock" engagement. Although an embodiment of the invention has been described where the temperature controllable switch includes a thermistor and transistor arrangement other temperature sensors may be utilised such as a thermocouple or resistance temperature detector (RTD).

One or more embodiments in accordance with the present invention may be configured to utilise an inhaler having a similar shape and aspect ratio as a Nicorette® inhaler and consequently a Nicorette® capsule may be utilised in such an inhaler. Although a capsule such as a Nicorette® capsule may be the most convenient support for substrate 14, embodiments are envisaged in which substrate 14 is supported directly in the inhaler without being surrounded by capsule 10.

Although an embodiment utilising an exothermic reaction has been described in which sodium bicarbonate solution and calcium chloride are mixed together, other suitable exothermic reactions may be utilised to provide a temperature increase up to around 40° C. for a duration of around five minutes.

The scope of the present disclosure includes any novel feature or combination of features disclosed therein either explicitly or implicitly or any generalisation thereof irrespective of whether or not it relates to the claimed invention or mitigate against any or all of the problems addressed by the present invention. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

The invention claimed is:

1. An inhaler comprising:
an assembly including:
a main body having a mouthpiece provided at an upstream end and a side wall, the main body extending along a principal axis;
a substrate region of the main body configured to receive and support a capsule, the capsule containing vapour and/or atomizer precursor substrate, wherein the capsule is sealed by an end seal at an end of the capsule, and wherein the substrate region includes a plurality of prongs at an end of the substrate region, the plurality of prongs extending from the side wall of the main body and angled towards the principal axis of the main body, the plurality of prongs being arranged to rupture the end seal of the capsule, the plurality of prongs together defining a single aperture extending along the principal axis between the plurality of prongs and configured such that, through said aperture, vaporized or atomized substance from said precursor substrate is capable of being drawn into the mouthpiece; and
a heater element arranged in the inhaler to be proximal to the substrate region, wherein the mouthpiece is arranged in fluid communication with the aperture;
wherein the assembly is configured such that the heater element is operative to achieve and maintain a target temperature in the substrate region throughout a period corresponding to a plurality of consecutive uses of the inhaler.

2. The inhaler according to claim 1, wherein the heater element is an electrical heater element.

3. The inhaler according to claim 1, further comprising a temperature controllable switch configured to control the heater element to achieve and maintain the target temperature throughout the period.

4. The inhaler according to claim 3, the assembly further comprising a temperature sensor operative to provide a signal to the temperature controllable switch indicative of a temperature in the substrate region.

5. The inhaler according to claim 4, wherein the assembly is configured such that the temperature controllable switch is integral with the temperature sensor.

6. The inhaler according to claim 4, wherein the temperature sensor is a one of a thermistor, thermocouple, and resistance temperature detector (RTD).

7. The inhaler according to claim 4, 5, or 6, wherein the assembly is arranged such that the temperature sensor is disposed proximal to where the capsule is to be supported in the inhaler.

8. The inhaler according to claim 3, wherein the temperature controllable switch is operative to couple and/or decouple the heater element from an electrical current source to achieve and maintain the target temperature throughout the period.

9. The inhaler according to claim 3, wherein the temperature controllable switch comprises a bi-metal strip.

10. The inhaler according to claim 3, wherein the temperature controllable switch is an electrical switch.

11. The inhaler according to claim 1, wherein the assembly is arranged such that the heater element is disposed proximal to where the capsule is to be supported in the inhaler.

12. The inhaler according to claim 1, wherein the heater element is arranged to define an interior space into which the substrate may be inserted.

13. The inhaler according to claim 1, wherein the heater element is arranged to define an interior space into which the capsule may be inserted.

14. The inhaler according to claim 1, further comprising a current source.

15. The inhaler according to claim 14, wherein the assembly comprises the current source.

16. The inhaler according to claim 14, wherein the current source is an electrical battery.

17. The inhaler according to claim 1, wherein the heater element comprises a partitioned container having respective partitions comprising constituent elements which when brought together create an exothermic reaction.

18. The inhaler according to claim 1, wherein the assembly is configured such that the period lies in the range of 2 minutes to 8 minutes.

19. The inhaler according to claim 1, wherein the assembly is configured such that the heater element is operative to achieve and maintain the target temperature in the range from 20° C. to 50° C.

20. The inhaler according to claim 1, wherein the assembly is configured such that the heater element is responsive to an input to initiate heating of the substrate region to the target temperature.

21. The inhaler according to claim 20, wherein the input is a manual input.

22. A substrate for an inhaler of claim 1, wherein the vapour and/or atomiser precursor comprises one or more of nicotine, a nicotine derivative, and nicotine analogue.

23. The substrate according to claim 22, wherein the substrate is hydrophilic.

24. The substrate according to claim 22, wherein the substrate comprises a sintered material.

25. The substrate according to claim 22, wherein the substrate comprises polypropylene or polyethylene terephthalate.

26. A substrate for an inhaler according to claim 1, wherein the vapour and/or atomiser precursor comprises one or more of a glycol, polyglycol, and water.

27. A capsule for an inhaler according to claim 1, wherein the capsule encloses a vapour and/or atomizer precursor substrate, the vapour and/or atomizer precursor substrate comprising:
   one or more of nicotine, a nicotine derivative, and nicotine analogue, or
   one or more of a glycol, polyglycol, and water.

28. The inhaler according to claim 1, wherein the vapour and/or atomizer precursor substrate comprises:
   one or more of nicotine, a nicotine derivative, and nicotine analogue, or
   one or more of a glycol, polyglycol, and water.

29. A vapour and/or atomiser inhaler device comprising an inhaler according to claim 1.

30. The vapour and/or atomiser inhaler device according to claim 29, operative as a smoking substitute device.

* * * * *